United States Patent
Oshemkov et al.

(10) Patent No.: US 8,101,921 B2
(45) Date of Patent: Jan. 24, 2012

(54) APPARATUS AND METHOD FOR INDUCING CONTROLLABLE JETS IN LIQUIDS

(75) Inventors: Sergey Oshemkov, Karmiel (IL); Vladimir Dmitriev, Karmiel (IL); Lev Dvorkin, Akko (IL)

(73) Assignee: Carl Zeiss SMS Ltd, Karmiel (IL)

( * ) Notice: Subject to any disclaimer, the term of this patent is extended or adjusted under 35 U.S.C. 154(b) by 903 days.

(21) Appl. No.: 12/133,004

(22) Filed: Jun. 4, 2008

(65) Prior Publication Data
US 2009/0000665 A1    Jan. 1, 2009

Related U.S. Application Data

(60) Provisional application No. 60/924,881, filed on Jun. 4, 2007.

(51) Int. Cl.
*G21K 5/00* (2006.01)
*H01S 3/09* (2006.01)
*G05D 7/06* (2006.01)

(52) U.S. Cl. ...... 250/423 R; 250/435; 137/13; 137/827; 137/830; 261/28; 606/2

(58) Field of Classification Search ............... 137/13, 137/827, 830; 250/423 R, 435; 261/28; 606/2
See application file for complete search history.

(56) References Cited

U.S. PATENT DOCUMENTS

| 5,037,431 | A | 8/1991 | Summers et al. |
| 6,029,912 | A | 2/2000 | Woolley |
| 6,566,626 | B2 | 5/2003 | Gaissinsky et al. |
| 6,777,642 | B2 | 8/2004 | Song et al. |
| 6,960,307 | B2 * | 11/2005 | LeClair ............ 216/52 |
| 7,100,846 | B2 | 9/2006 | Pein |
| 7,297,288 | B1 * | 11/2007 | LeClair ............ 216/83 |
| 2004/0004055 | A1 | 1/2004 | Barros |
| 2005/0003737 | A1 | 1/2005 | Montierth |
| 2005/0064137 | A1 | 3/2005 | Hunt et al. |
| 2006/0029525 | A1 | 2/2006 | Laugharn, Jr. et al. |
| 2011/0036991 | A1 * | 2/2011 | Oshemkov et al. ....... 250/432 R |

OTHER PUBLICATIONS

E.A. Brujan et al. "Dynamics of Laser-induced cavitation bubbles near boundaries: Influence of elastic modules" Journal of Fluid Mech. 433, pp. 283-314, Feb. 21, 2000.
International Search for Application No. PCT/IL2008/000755 Dated: Nov. 10, 2008.

* cited by examiner

*Primary Examiner* — Nikita Wells
(74) *Attorney, Agent, or Firm* — Pearl Cohen Zedek Latzer, LLP

(57) ABSTRACT

A method for inducing a controllable jet in a transparent liquid is disclosed. The method comprises providing a gas-liquid interface, providing a laser source and generating a beam comprising a sequence of laser pulses, and focusing the beam to a target location within the liquid at a predetermined distance from the gas-liquid interface and creating a plurality of cavitation bubbles, yielding a jet directed away from the gas-liquid interface. Other methods and apparatus are also described and claimed.

21 Claims, 11 Drawing Sheets

APPARATUS AND METHOD FOR INDUCING CONTROLLABLE JETS IN LIQUIDS

This application claims the benefit under 35 U.S.C. §119 (e) of U.S. Provisional Patent Application No. 60/924,881, filed Jun. 4, 2007.

FIELD OF THE INVENTION

The present invention relates to the creation of jets in liquids. More specifically, the present invention relates to laser induced controllable jets in liquids.

BACKGROUND OF THE INVENTION

Several patents disclose various nozzle type liquid jet devices, which are described hereinafter.

U.S. Pat. No. 7,100,846 (Pein) discloses a water-jet device for separating a biological structure. The separating nozzle is furnished with a nozzle channel, with the nozzle channel provided with one or several twisted grooves at the circumference of the nozzle channel and wherein the number of the twisted grooves and the diameter and the length of the nozzle channel are placed in such ratio that the separating jet subjected to pressure is rotated.

U.S. Pat. No. 5,037,431 (Summers et al) discloses a hand-held surgical apparatus with supporting equipment comprising a mechanism for producing a pressurized jet of fluid which is sufficiently energetic to fragment diseased human and animal tissue without damaging adjacent healthy tissue. Preferably the apparatus includes a jet of fluid which impinges obliquely onto the operative area such that diseased tissue underneath overlying healthy tissue may be fragmented, especially finger-like extensions from tumorous growths of the skin. The jet rotated about a generally vertical axis such that the points of impact of the water from the jet upon the operative area describe circular patterns, thereby effectively and quickly distributing fragmenting energy over a wide operative area. A supporting vacuuming apparatus for aspirating effluent or expended fluid and fragmented tissue from the operative site. A surgical procedure for removing tumorous growths at the cutaneous surface includes the steps of impinging a growth on the skin with a jet of pressurized fluid using the apparatus.

U.S. Pat. No. 6,029,912 (Woolley) discloses a device for producing a stream of aerated water, the device having a first opening for producing a first jet of water and a second opening for producing a second jet of water directed into the first jet of water so as to form a single turbulent stream of water in which air is entrained. The device being constructed by forming two relatively angled surfaces on at least one component, the surfaces having respective aligned grooves, forming two oppositely angled surfaces on at least one other component and mounting the two relatively angled surfaces against the two oppositely angled surfaces such that the grooves, together with the oppositely angled surfaces define passages for the formation of jets of water.

A disadvantage associated with the above mentioned devices and methods is their inability to produce a sterile jet with a diameter in the micrometer range.

Laser induced micro-flows in liquids partially overcome this problem.

Previous studies and investigations show that focusing a laser beam inside a liquid may lead to emission of gas bubbles and micro flows of liquid originating at the focal point of the laser beam. These bubbles and micro flows are typically generated in an irregular and uncontrolled manner.

When high power laser radiation is tightly focused inside liquid, it generates hot plasma assisted by the formation of shock wave and gas bubbles (i.e., cavitation bubbles) with various diameters, emitted from the focal point. The breakdown is initiated by multiphoton or avalanche ionization of molecules of the liquid.

The phenomenon of bubbles and micro flows formation by laser radiation focused in the liquid volume was used by various investigators including Song et al (U.S. Pat. No. 6,777,642) who discloses an apparatus and a method for producing a relatively sterile jet and E. A. Brujan et al, "Dynamics of laser-induced cavitation bubbles near elastic boundaries: influence of the elastic modulus", *Journ. of Fluid Mech.*, 433, p. 283, 2001, who investigated the interaction of a single laser-induced cavitation bubble with an elastic boundary experimentally by high-speed photography and acoustic measurements.

Song et al discloses a laser-based apparatus and method for cleaning solid surfaces immersed in liquids. Such solids include a Si substrate, a disk or a magnetic head slider where contaminants, including organic contaminants, especially particles in the micron or sub-micron scale are effectively removed from the solid surfaces.

Song et al. achieve this by generating a strong laser-induced liquid jet and shock wave near the solid surfaces immersed in liquid. The liquid is a solution of water and other solvents to help reduce adhesion force and enhance cleaning efficiency.

Thus, Song et al allow the creation of a relatively sterile jet. However, the apparatus and method of Song et al. fail to create a jet with a diameter in the micrometer range.

Similarly, E. A. Brujan et al were limited to use single nanosecond laser pulses in their investigations of laser induced breakdown in liquids.

Since jets induced by high repetition rate laser pulses as well as jets which are sterile and at the same time possessing a diameter in the micrometer range are highly desired and would be a great asset to the medical and biological fields, an aim of the present invention is to provide an apparatus and a method for creating a sterile jet with a diameter in the micrometer range or smaller which is induced by high repetition rate laser pulses.

Other advantages and aims of the present invention will become apparent after reading the present invention and reviewing the accompanying figures.

SUMMARY OF THE INVENTION

There is thus provided, in accordance with some embodiments of the present invention, a method for inducing a controllable jet in a transparent liquid, comprising:

providing a gas-liquid interface;

providing a laser source and generating a beam comprising a sequence of laser pulses; and focusing said beam to a target location within the liquid at a predetermined distance from the gas-liquid interface and creating a plurality of cavitation bubbles.

Furthermore, in accordance with some embodiments of the present invention, the step of generating a beam comprising a sequence of laser pulses includes generating laser pulses wherein each laser pulse is sufficient to create cavitation bubble.

Furthermore, in accordance with some embodiments of the present invention, the predetermined distance is chosen to keep integrity of the gas-liquid interface and yielding a jet directed away from the gas-liquid interface.

Furthermore, in accordance with some embodiments of the present invention, the sequence of laser pulses comprises pulses with wavelength in the range of 0.3 to 3 µm, having a pulse energy ranging from 0.01 µJ to 100 mJ, a pulse width ranging from 10 fs to 30 ns and repetition rate ranging from 1 Hz to 100 MHz.

Furthermore, in accordance with some embodiments of the present invention, a time interval between the laser pulses within said sequence of pulses is longer than the cavitation time of the bubble and less than the decay time of cavitation flow generated by each bubble.

Furthermore, in accordance with some embodiments of the present invention, the step of creating a plurality of cavitation bubbles comprises creating a plurality of cavitation bubbles, so that each bubble moves away from the target location before the next bubble is created.

Furthermore, in accordance with some embodiments of the present invention, the gas-liquid interface is an air-water interface.

Furthermore, in accordance with some embodiments of the present invention, the gas-liquid interface is a liquid vapor-liquid interface.

Furthermore, in accordance with some embodiments of the present invention, the gas-liquid interface is an inert gas-water interface.

Furthermore, in accordance with some embodiments of the present invention, the gas-liquid interface is substantially flat.

Furthermore, in accordance with some embodiments of the present invention, the gas-liquid interface is curved.

Furthermore, in accordance with some embodiments of the present invention, the step of providing the gas-liquid interface in the liquid comprises providing a transparent surface atop a container filled with the liquid and providing a gas bubble beneath the transparent surface, the gas bubble defining the gas-liquid interface.

Furthermore, in accordance with some embodiments of the present invention, the step of providing the gas-liquid interface in the liquid comprises providing a solid holder in a container filled with the liquid and providing a gas bubble fixed on said solid holder defining the gas-liquid interface.

Furthermore, in accordance with some embodiments of the present invention, the solid holder is a needle.

Furthermore, in accordance with some embodiments of the present invention, the step of providing the gas-liquid interface comprises providing a liquid drop on a surface, the liquid drop defining the gas-liquid interface.

Furthermore, in accordance with some embodiments of the present invention, the step of providing the gas-liquid interface comprises providing a capillary in a container filled with the liquid and a pump for inflating a gas bubble through said capillary creating the gas-liquid interface.

Furthermore, in accordance with some embodiments of the present invention, the method further comprises providing relative displacement between the target location and the gas-liquid interface for controlling the length and direction of propagation of the jet.

Furthermore, in accordance with some embodiments of the present invention, the method further comprises varying a property of the gas-liquid interface to control the jet.

Furthermore, in accordance with some embodiments of the present invention, the property of the gas-liquid interface is selected from a group of properties including curvature and distance from the target location.

Furthermore, in accordance with some embodiments of the present invention, there is provided an apparatus for inducing a controllable jet in a transparent liquid, the apparatus comprising:

a support of liquid with a gas-liquid interface;

a laser source for generating a beam comprising a sequence of laser pulses;

a focusing optics for focusing a said beam to a target location within the liquid at a predetermined distance for creating a plurality of cavitation bubbles, yielding a jet directed away from the gas-liquid interface; and a relative displacement facilitator for facilitating relative displacement between the objective focal point and the gas-liquid interface for setting a predetermined distance between the objective focal point and the gas-liquid interface.

Furthermore, in accordance with some embodiments of the present invention, the apparatus is further provided with a facilitator for varying a property of the gas-liquid interface selected from a group of properties including a curvature of the gas-liquid interface and the distance of the target location from the gas-liquid interface.

Furthermore, in accordance with some embodiments of the present invention, the sequence of laser pulses comprises pulses with wavelength in the range of 0.3 to 3 µm, having a pulse energy ranging from 0.01 µJ to 100 mJ, a pulse width ranging from 10 fs to 30 ns and repetition rate ranging from 1 Hz to 100 MHz.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF PREFERRED EMBODIMENTS

Figure 1:
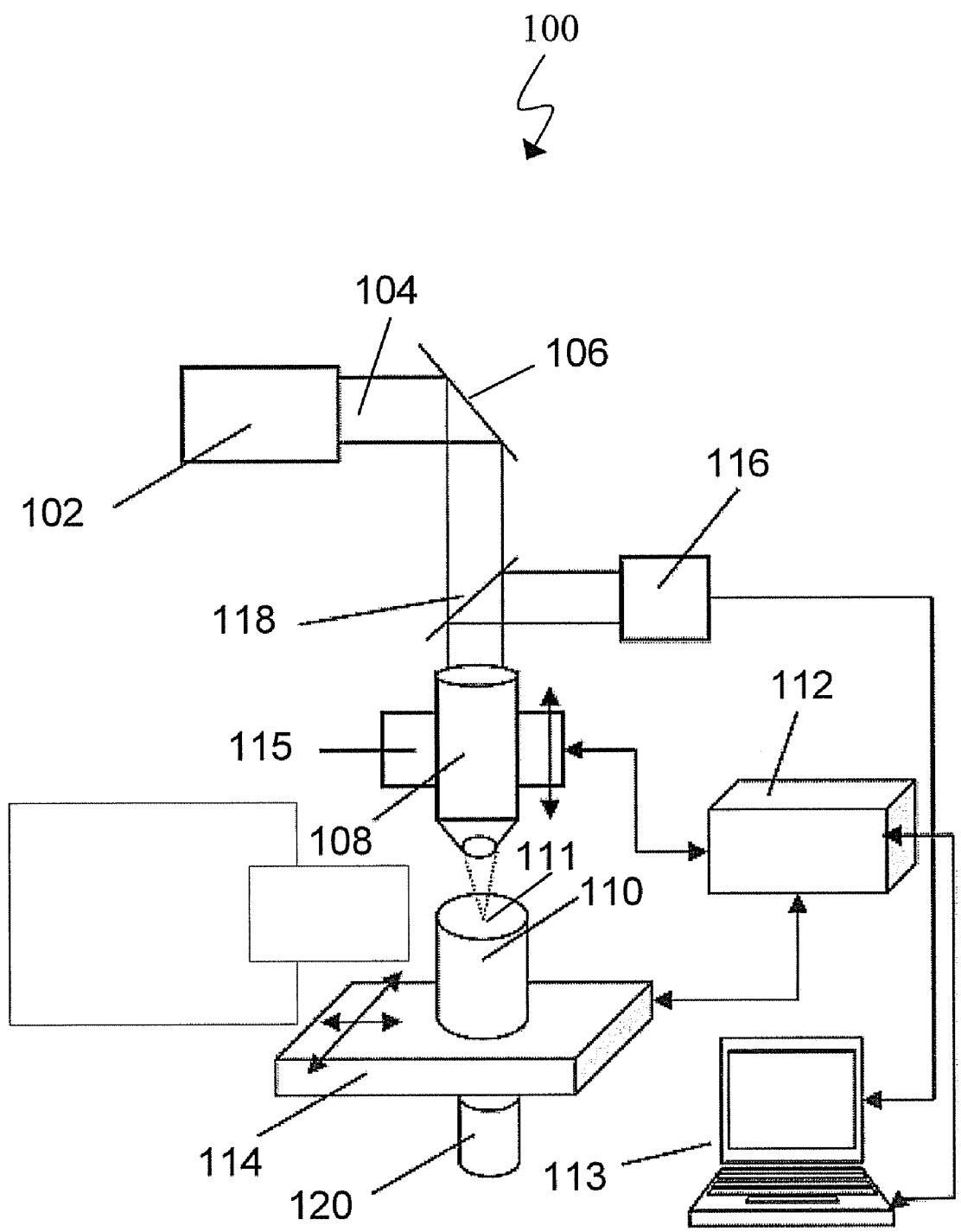
FIG. 1 is a block diagram of an apparatus for inducing a controllable jet in a liquid, in accordance with embodiments of the present invention.

In the following detailed description, numerous specific details are set forth in order to provide a thorough understanding of the invention. However it will be understood by those of ordinary skill in the art that the present invention may be practiced without these specific details. In other instances, well-known methods, procedures, components and circuits have not been described in detail so as not to obscure the present invention.

According to embodiments of the present invention a low divergence jet is created in liquid wherein the length and direction of the formed jet are controllable.

The inventors of the present invention have found that when a sequence of laser pulses with a high repetition rate is focused into liquid in the vicinity of a gas-liquid interface, a controllable jet is originated at the focal point e.g., at the target location of the laser beam and directed away from the gas-liquid interface.

The jet propagates along a direction determined by two parameters: (a) the center of curvature of the gas-liquid interface and (b) the target location of the laser beam. More specifically, the direction of the jet is substantially perpendicular to the tangent to the gas-liquid interface, passing through the target location of the laser beam.

The length of the jet depends on the kind of liquid, the laser energy, repetition rate of laser pulses, laser pulse width and on the distance between the target location of the laser beam and the gas-liquid interface, and under proper conditions, the jet length may reach several centimeters.

Laser pulses with wavelength in the range of 0.3 to 3 μm, having a pulse energy ranging from 0.01 μJ to 100 mJ, a pulse width ranging from 10 fs to 30 ns and repetition rate ranging from 1 Hz to 100 MHz were used in these experiments. However, laser pulses with a pulse energy, a pulse width, and a repetition rate not included in the above-mentioned ranges may be used as well for creating jets in liquids.

The liquid used in such experiments should be either fully transparent or at least partially transparent allowing laser radiation to penetrate the liquid and be focused at a predetermined target location.

The inventors succeeded in forming controllable laser-induced jets in various liquids including distilled water, tap water, water solutions of NaCl and sugar, heavy water and some organic liquids such as ethyl alcohol, methyl alcohol, acetone, butane and benzene.

In addition, the inventors succeeded in forming controllable laser-induced jets in the vicinity of various gas-liquid interfaces such as an air-water interface, a vapor-liquid interface, an inert gas-liquid interface and the like.

It is known from prior art that a cavitation bubble produced by a single laser pulse in liquid in the vicinity of a gas-liquid interface ejects a liquid jet directed away from the interface.

Cavitation time of the cavitation bubble can be calculated using Rayleigh's formula:

$$R_{max} = 1.09[(p-p_v)/?]^{0.5} * t_c,$$

where $t_c$—time of bubble collapse,
$R_{max}$—the maximum radius of a cavitation bubble,
$p$—the ambient pressure,
$p_v$—the vapor pressure, and
$\rho$—the density of the liquid Under the used experimental conditions, the inventors have found that each laser pulse creates a single cavitation bubble which collapses prior to the next generated laser pulse and adds to the formation of a micro-flow of liquid. In addition, when the decay time of each micro-flow of liquid exceeds the repetition period of the laser pulses, two or more of such micro-flows combine to form a jet characterized by a length which keeps increasing as long as laser pulses are provided.

It should be noted that the length of the jet is limited by energy losses associated with viscous friction in the liquid.

Based on their observations, the inventors concluded that the conditions required for producing a jet by a sequence of laser pulses focused into liquid in the vicinity of a gas-liquid interface include: (a) generating a beam which comprises a sequence of laser pulses wherein each laser pulse is sufficient to create a single cavitation bubble, (b) choosing a predetermined distance so that the integrity of the gas-liquid interface is kept, (c) creating a plurality of cavitation bubbles so that each bubble moves away from the target location before the next bubble is created, and (d) the time interval between two cavitation bubbles formation should be longer than the cavitation time of the bubble and less than the decay time of cavitation flow generated by each bubble.

FIG. 1 is a block diagram of an apparatus 100 for inducing a controllable jet in a liquid 110, in accordance with embodiments of the present invention.

Apparatus 100 includes pulse laser source 102 for producing a pulsed laser beam 104, a steering mirror 106 for directing pulsed laser beam 104 and focusing objective 108 for focusing pulsed laser beam 104 into liquid 110.

Apparatus 100 also includes controller 112 and computer 113 for directing two-axis positioning stage 114 which manages translations in X and Y directions and one-axis positioning stage 115 which manages translations in a Z direction for moving liquid 110 and target location 111 of pulsed laser beam 104 to a desired relative position.

It should be noted that manual stages can also be used for translating liquid 110 and target location 111 of pulsed laser beam 104 in X, Y and Z directions.

Apparatus 100 may also provide a viewing system including CCD camera 116, dichroic mirror 118 and bottom illumination source 120 which facilitates navigation of the target location 111 to the proximity of the gas-liquid interface and observation on formation of bubbles and jets in the liquid.

It should be noted that jets with diameters other than in the order of microns may also be induced by an apparatus according to embodiments of the present invention.

Figure 2:
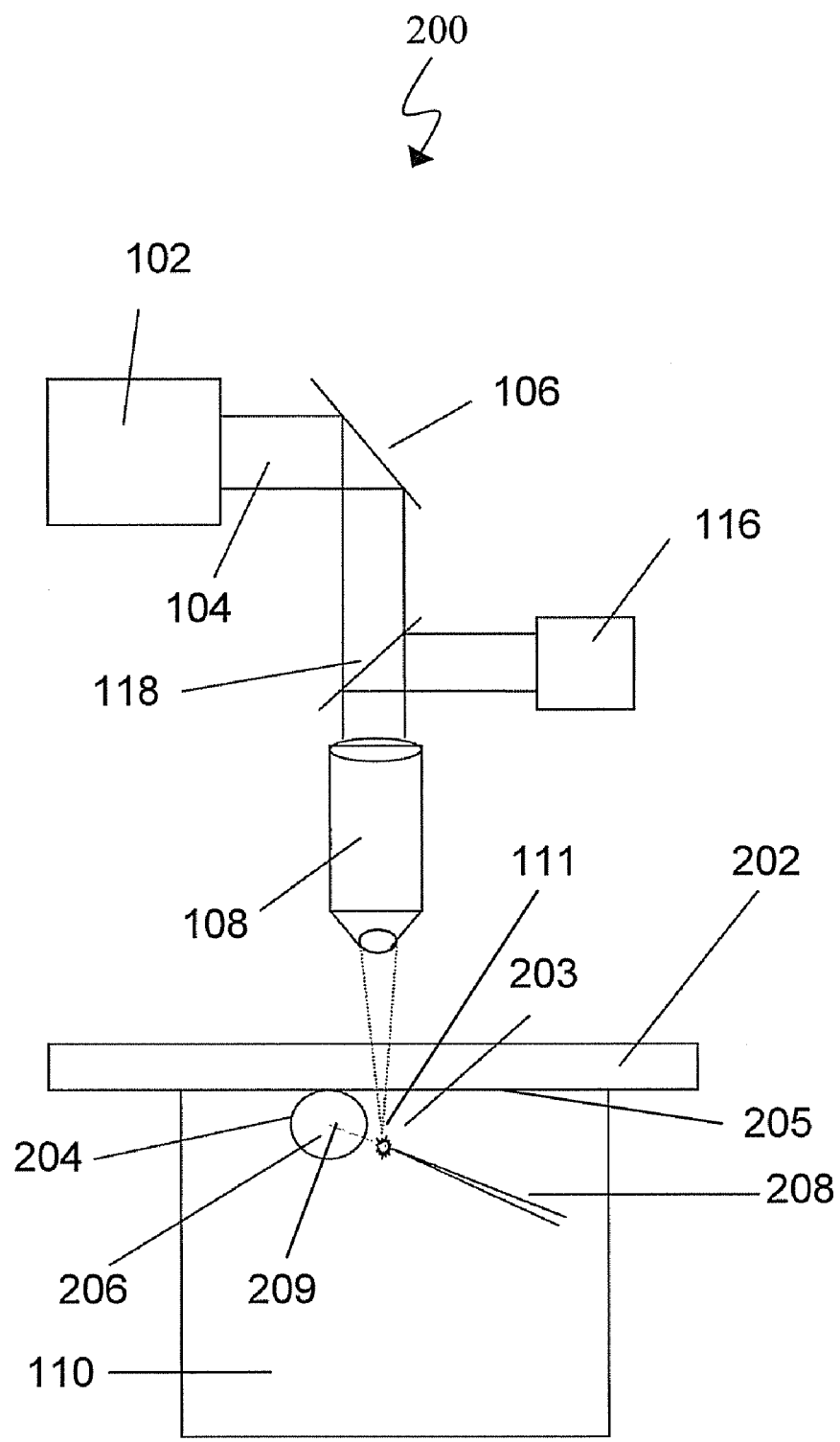
FIG. 2 illustrates an apparatus for inducing a controllable jet in accordance with preferred embodiments of the present invention.

FIG. 2 illustrates an apparatus 200 for inducing a (controllable) jet 208 in accordance with embodiments of the present invention.

Pulsed laser beam 104 is focused by objective 108 through transparent solid surface 202 which can, for example, be made of glass, fused silica, plastic and the like to predetermined target location 203 inside liquid 110.

Predetermined target location 203 is in proximity to gas-liquid interface 204 formed by gas bubble 206 in liquid 110 where gas bubble 206 is fixed beneath a transparent solid surface 202, which is in full contact with liquid surface 205.

In case that target location 111 of pulsed laser beam 104 is in the vicinity of gas-liquid interface 204, jet 208 is induced in liquid 110 and propagates along line 209 which connects the center of gas bubble 206 and target location 111 of pulsed laser beam 104.

It should be noted that bubble 206 can be created in various ways. These include, for instance, laser breakdown in liquid in the mode of irregular emission of gas bubbles, which is known and had been described in prior art and the use of a solid holder such as a capillary tube (a needle for instance) for inserting a gas bubble into liquid under a transparent solid surface.

In addition, a pump can be used for inflating a gas bubble through the capillary for creating a gas-liquid interface.

In general, the propagation direction of an induced jet coincides with the direction of the normal to a gas-liquid interface of a gas bubble, passing through the objective focal point. As the distance between the focal point of pulsed laser beam 104 and the gas-liquid interface decreases, the length of the induced jet increases.

Thus, the propagation direction and the length of the produced jet are controllable and can be manipulated by changing the target location at which the laser beam is focused with respect to the gas-liquid interface formed by the gas bubble in the liquid and by changing the shape of the gas-liquid interface (e.g., changing the curvature of the gas-liquid interface).

The direction of propagation and the length of a induced jet also depend on physical parameters such as the liquid type, the energy of the laser pulse, pulse repetition rate, and pulse width.

Figure 3:
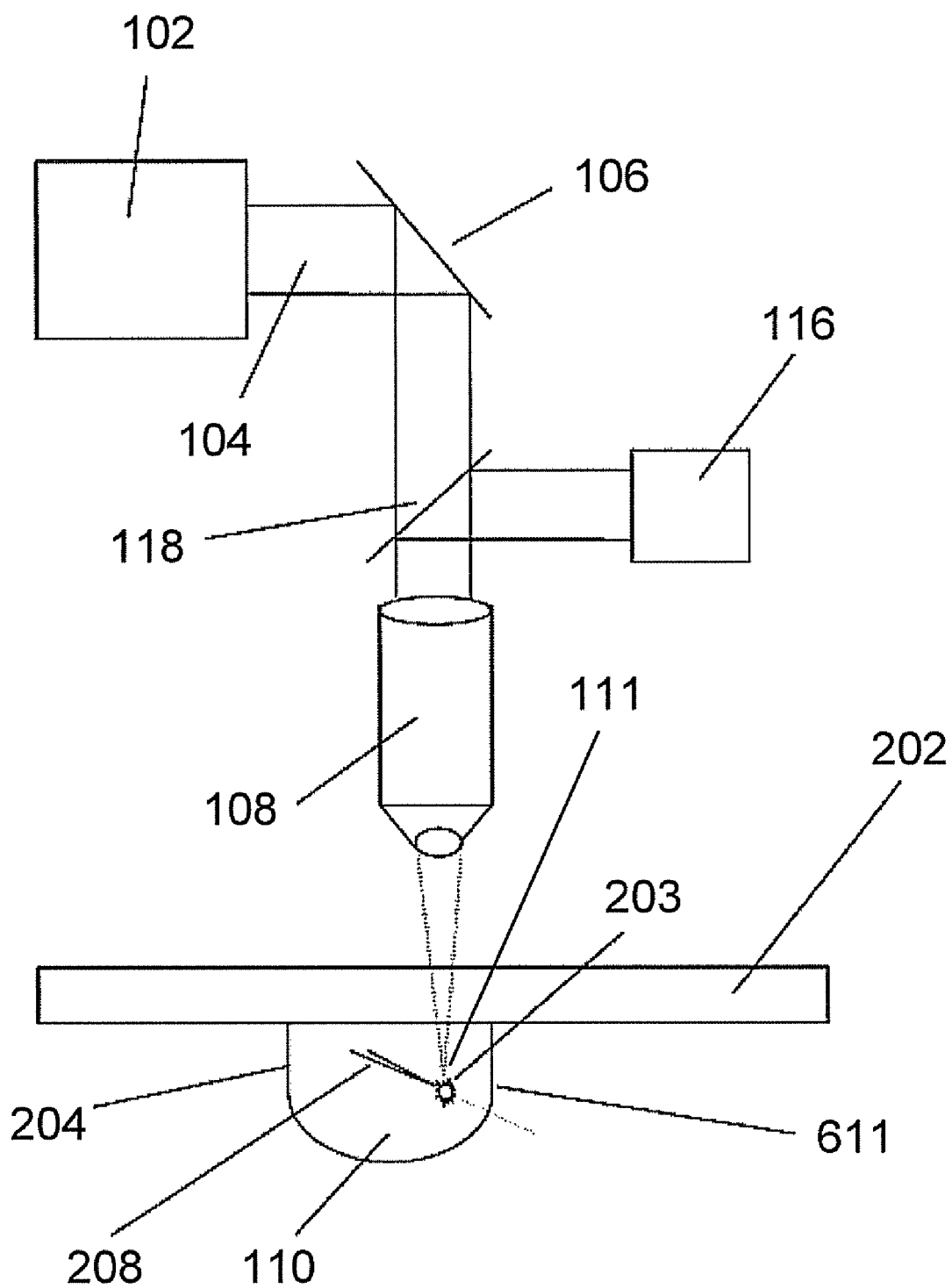
FIG. 3 illustrates an induction of a controllable jet in liquid near a curved gas-liquid interface defined by a liquid drop fixed beneath a surface in accordance with embodiments of the present invention.

FIG. 3 illustrates induction of a (controllable) jet 208 in liquid 110 near a curved gas-liquid interface 204 defined by a pendant liquid drop 611 (i.e., fixed beneath solid surface 202) in accordance with embodiments of the present invention.

Pulsed laser beam 104 is focused by objective 108 through transparent solid surface 202 such as, for example, glass, fused silica, plastic and the like, to a predetermined target location 203 inside liquid 110 close to gas-liquid interface 204.

In case that the target location 111 of pulsed laser beam 104 is in the vicinity of the gas-liquid interface 204, jet 208 appears in liquid 110. Jet 208 propagates along the perpendicular to gas-liquid interface 204 passing trough target location 111 of pulsed laser beam 104.

The direction of propagation and the length of jet 208 depend on the distance between target location 111 of pulsed laser beam 104 and gas-liquid interface 204, the shape of gas-liquid interface 204 and, as noted hereinabove, on physical parameters such as the liquid type, laser pulse energy, pulse repetition rate, and pulse width.

Figure 4:
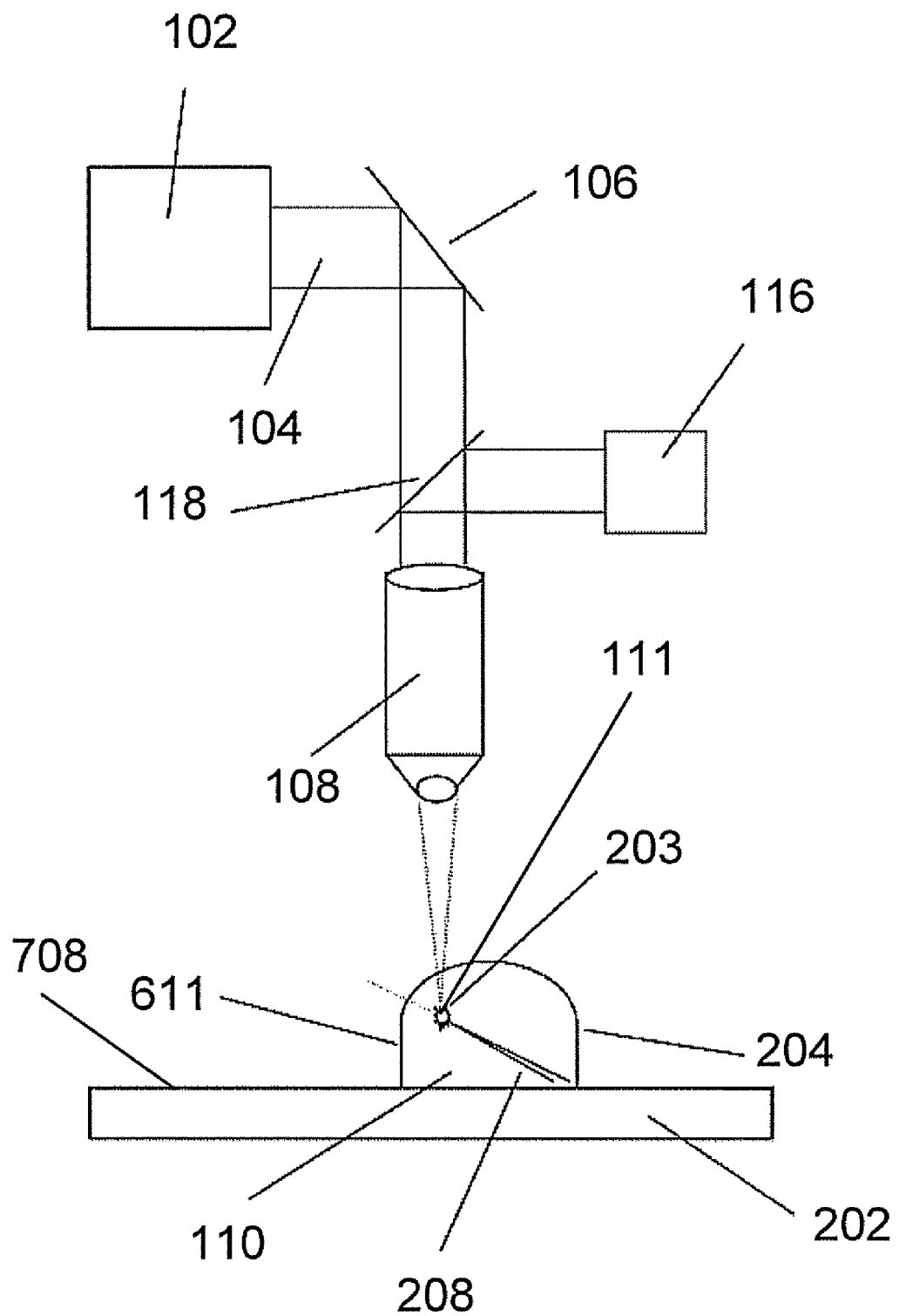
FIG. 4 illustrates induction of a controllable jet in liquid near a curved gas-liquid interface provided by a liquid drop atop a surface in accordance with embodiments of the present invention.

FIG. 4 illustrates induction of a controllable jet 208 in liquid 110 near a curved gas-liquid interface 204 provided by a liquid drop 611 situated on top of a surface 202 in accordance with embodiments of the present invention.

Pulsed laser beam 104 is focused by objective 108 to a predetermined target position 203 inside liquid 110 close to gas-liquid interface 204.

In case that the target location 111 of pulsed laser beam 104 is in the vicinity of gas-liquid interface 204, jet 208 appears in liquid 110. Jet 208 propagates along the perpendicular to gas-liquid interface 204 passing trough the target location 111 of pulsed laser beam 104.

The direction of propagation and the length of jet 208 depend on the distance between target location 111 of pulsed laser beam 104 and gas-liquid interface 204, the shape of gas-liquid interface 204 and as noted earlier on physical parameters such as the liquid type, laser pulse energy, pulse repetition rate, and pulse width.

In some embodiments of the present invention a bottom illumination source may be used for facilitating navigation of the focal point, therefore, surface 202 may be transparent. In other embodiments of the present invention, a side illumination source may be used and thus surface 202 may not necessarily be transparent.

Figure 5:
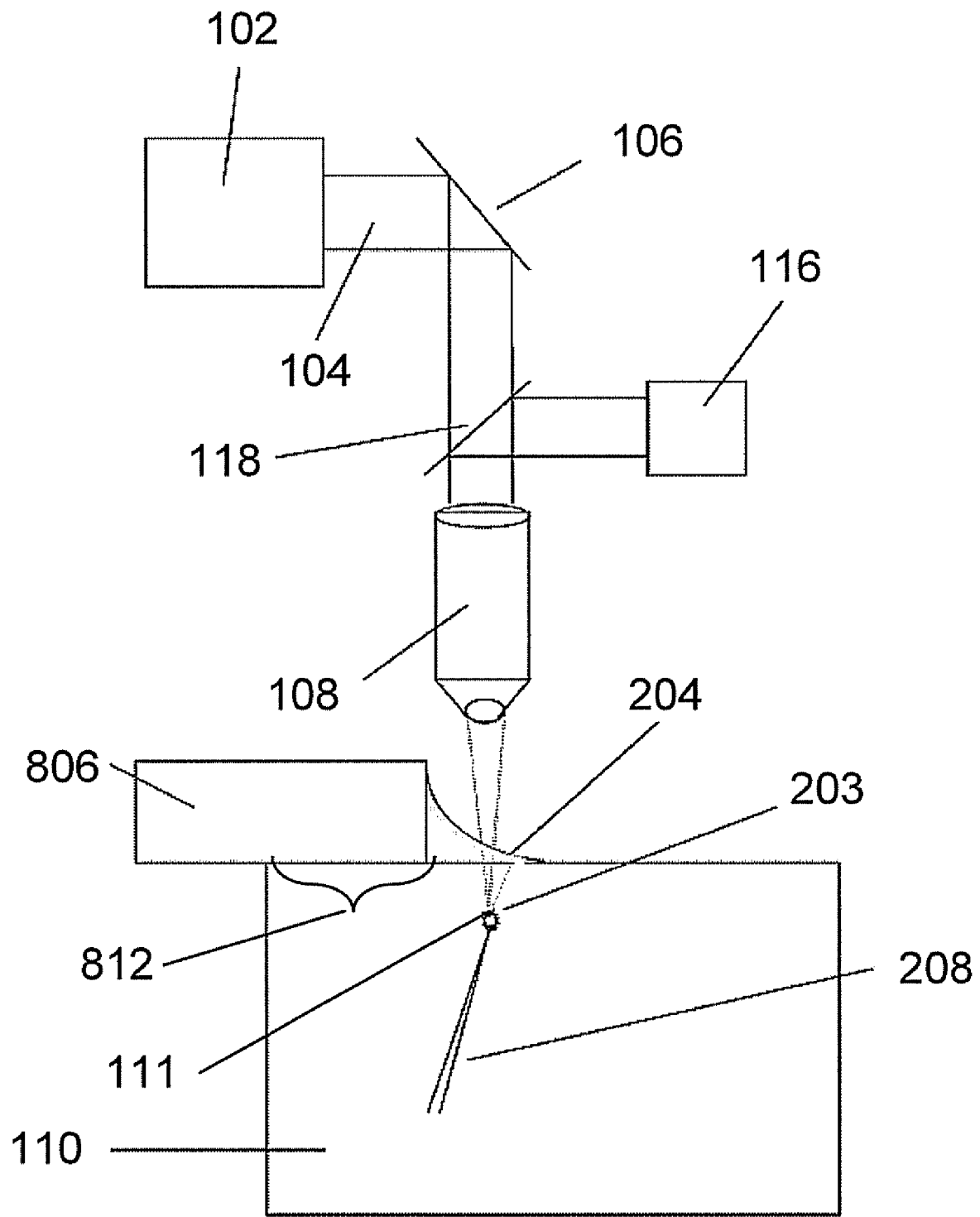
FIG. 5 illustrates induction of a controllable jet in liquid near a curved gas-liquid interface created in the vicinity of a solid surface in accordance with embodiments of the present invention.

FIG. 5 illustrates induction of a (controllable) jet 208 in liquid 110 near a curved gas-liquid interface 204 created in the vicinity of a solid surface 806 in accordance with embodiments of the present invention.

In this case, solid surface 806 is positioned on top of (and fully contacts) the upper surface of portion 812 of liquid 110.

pulsed laser beam 104 is focused by objective 108 to a predetermined target position 203 inside liquid 110 close to gas-liquid interface 204 curved by surface tension forces in the vicinity of a surface of solid surface 806.

Jet 208 appears and propagates along the perpendicular to the gas-liquid interface 204 passing trough target location 111 of pulsed laser beam 104.

The direction of propagation and the length of jet 208 depend on the position of target location 111 of pulsed laser beam 104 relative to gas-liquid interface 204, on the shape of gas-liquid interface 204 and on physical parameters such as the liquid type, energy of the laser pulse, pulse repetition rate, and pulse width.

Figure 6:
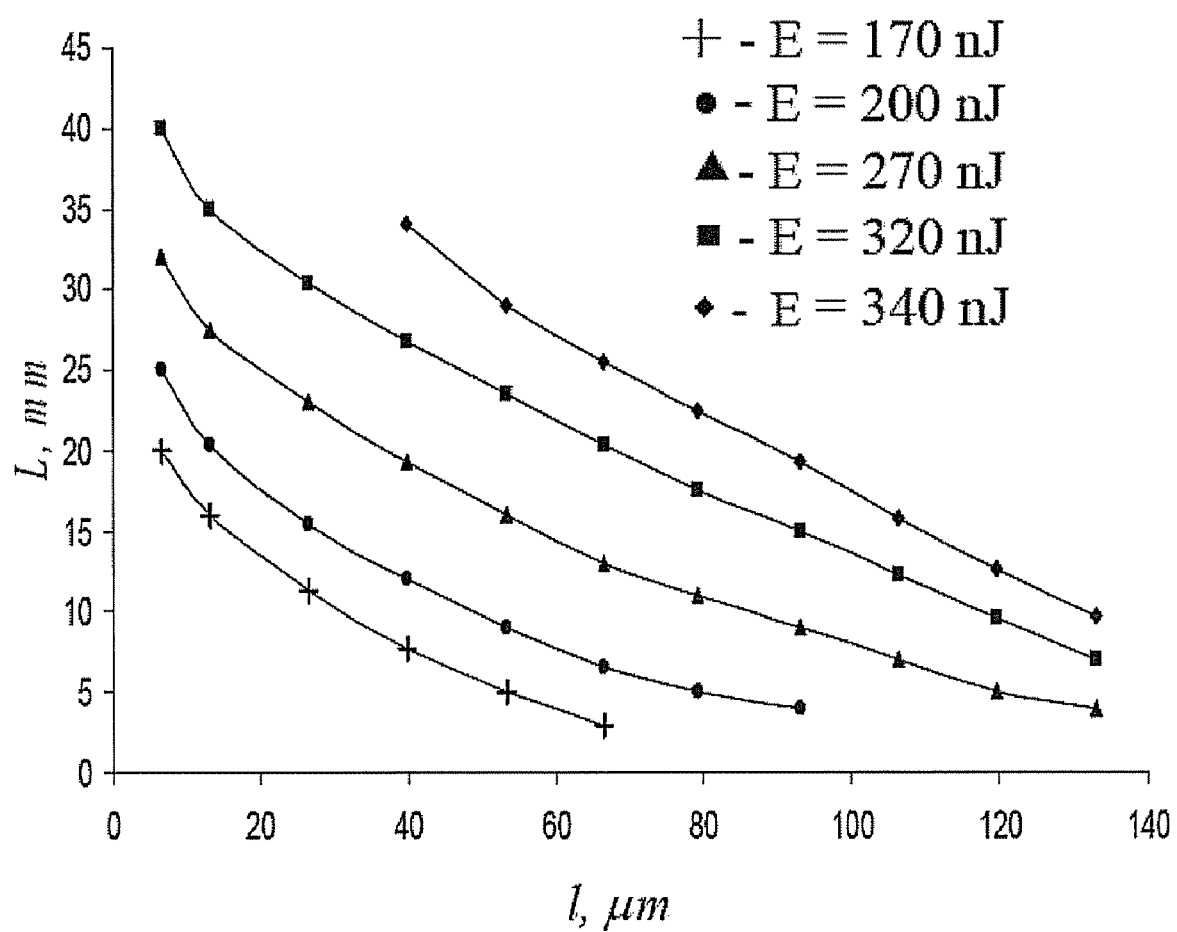
FIG. 6 is a chart illustrating the jet length (L) dependence on the laser pulse energy and on the distance (l) between the target location of the pulsed laser beam and the air-water interface.

FIG. 6 is a chart illustrating the jet length (L) dependence on the laser pulse energy and on the distance (l) between the target location of the pulsed laser beam and the air-water interface.

As is evident form that chart, the jet length increases as the distance between the target location of pulsed laser beam, and the air-water interface decreases, and with an increase in the laser pulse energy.

The distance (l) is characterized by the dimension-less parameter $\xi = l/R_{max}$, where l is the distance between the center of the cavitation bubble and the gas-liquid interface, and $R_{max}$ is the maximum radius of the cavitation bubble.

When a laser pulse energy of 170 nJ is used, a jet is created only in cases wherein the distance (l) is between 5 and 70 μm. Further movement of the target location of the pulsed laser beam away from the air-water interface (l>70 μm) leads to the formation of bubbles of irregular character instead of a jet.

Similarly, focusing of the laser beam to the target location very close to the air-water interface (l<5 μm) cause a damage of the air-water interface due to interaction with cavitation bubble and thus a jet is not formed.

When relatively high laser pulse energy of 340 nJ is used, a jet is created only when the target location of the pulsed laser beam is approximately 40 μm away from the air-water interface. This is due to the fact that at pulse energy of 340 nJ, which is much higher than the pulse energy threshold of cavitation bubble formation in distilled water, the air-water interface gets damaged as a result of interaction with cavitation bubble.

Thus, keeping the integrity of the gas-liquid interface determines the lower limit of the range of $\xi$ values while the upper limit of the range of $\xi$ values is determined by the interaction forces between the cavitation bubble and the gas-liquid interface wherein such forces values are determined by the kind of liquid used. In the case of distilled water, for instance, the dimension-less parameter $\xi$ should be within the range $0.1 < \xi < 10$.

Thus, the formation of a steady jet depends on physical properties of the used liquid such as for instance viscosity, surface tension, and the like as well as on the laser pulse wavelength, pulse energy, pulse width, and pulse repetition rate.

Figure 7:
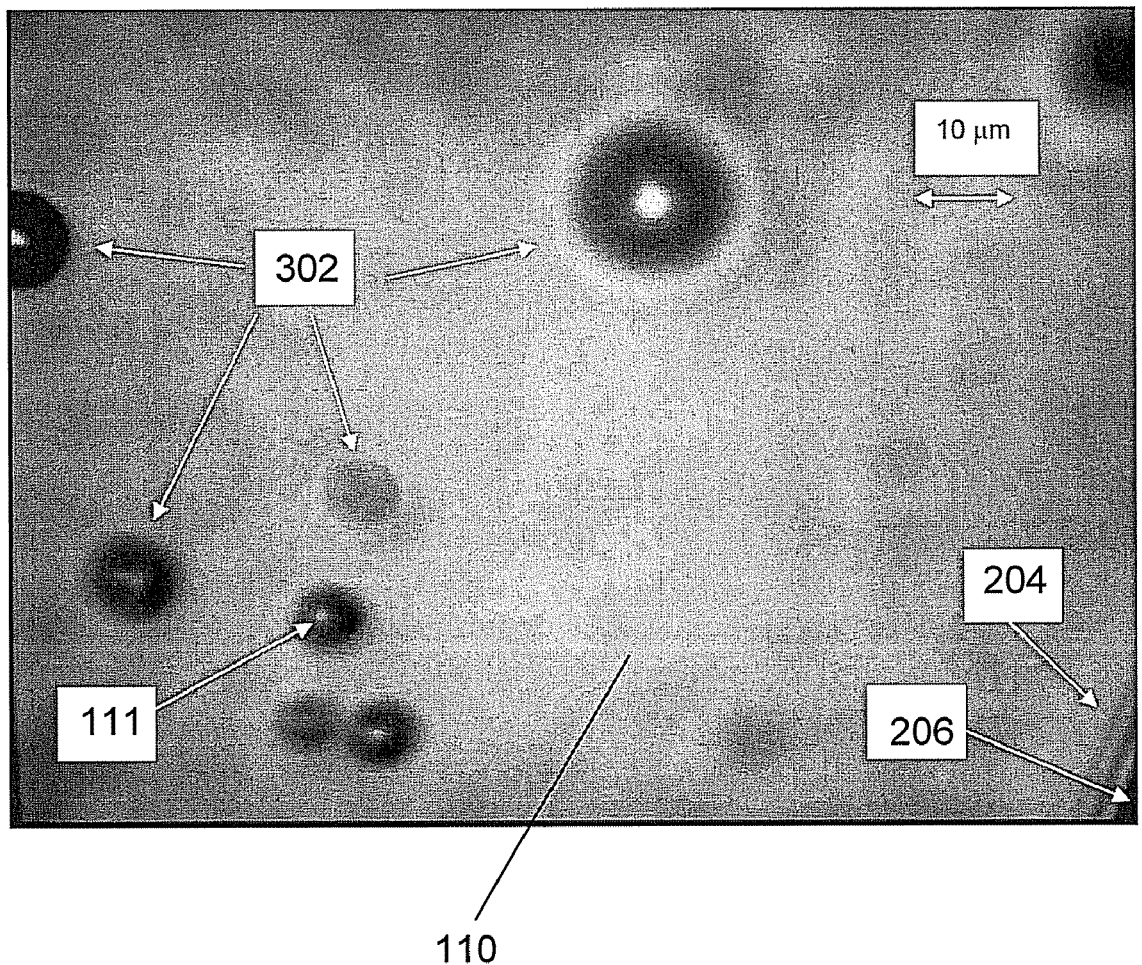
FIG. 7 illustrates a typical scenario of breakdown in liquid and the formation of cavitation bubbles with an irregular character.
Figure 8:
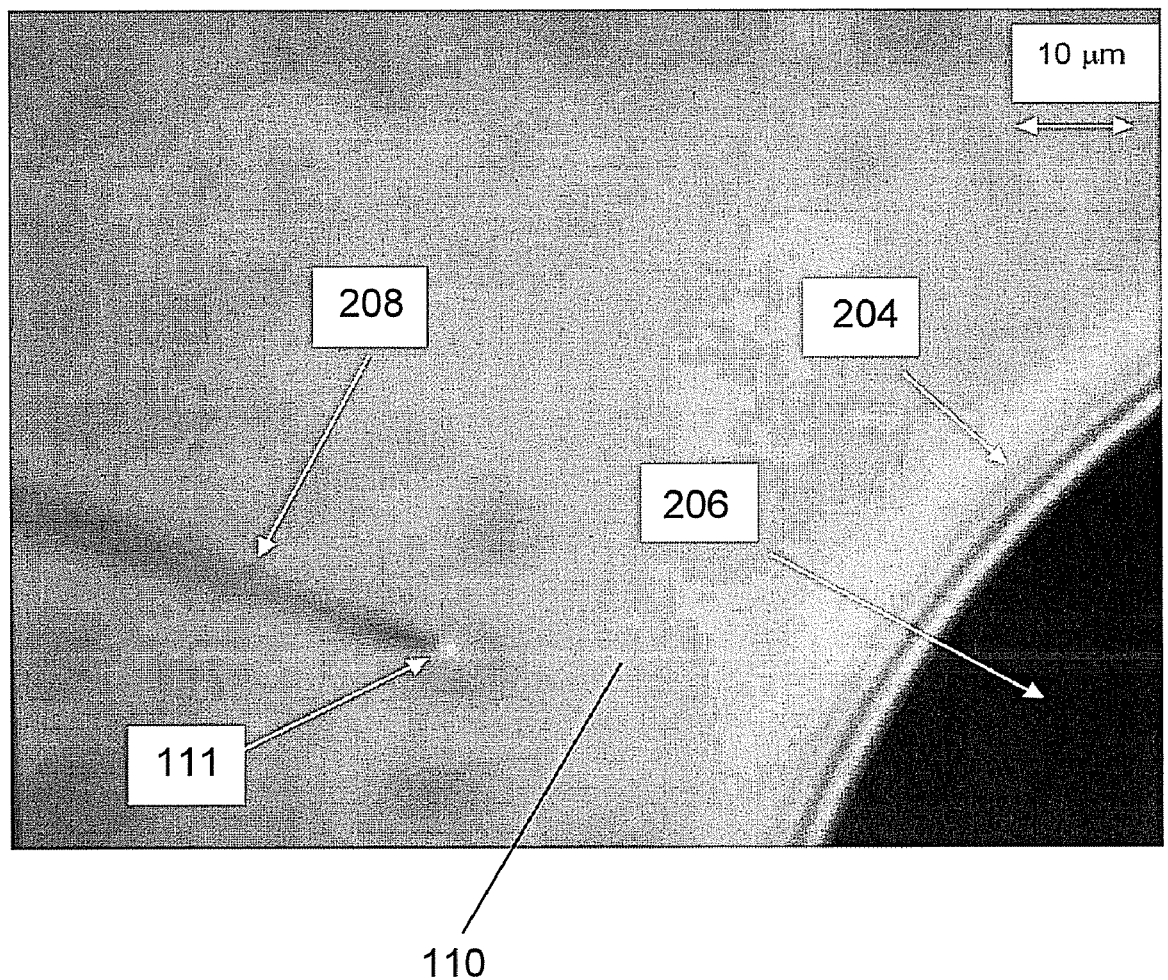
FIG. 8 illustrates a typical scenario of jet formation in liquid wherein the target location of the laser beam is about 40 µm away from gas-liquid interface.
Figure 9:
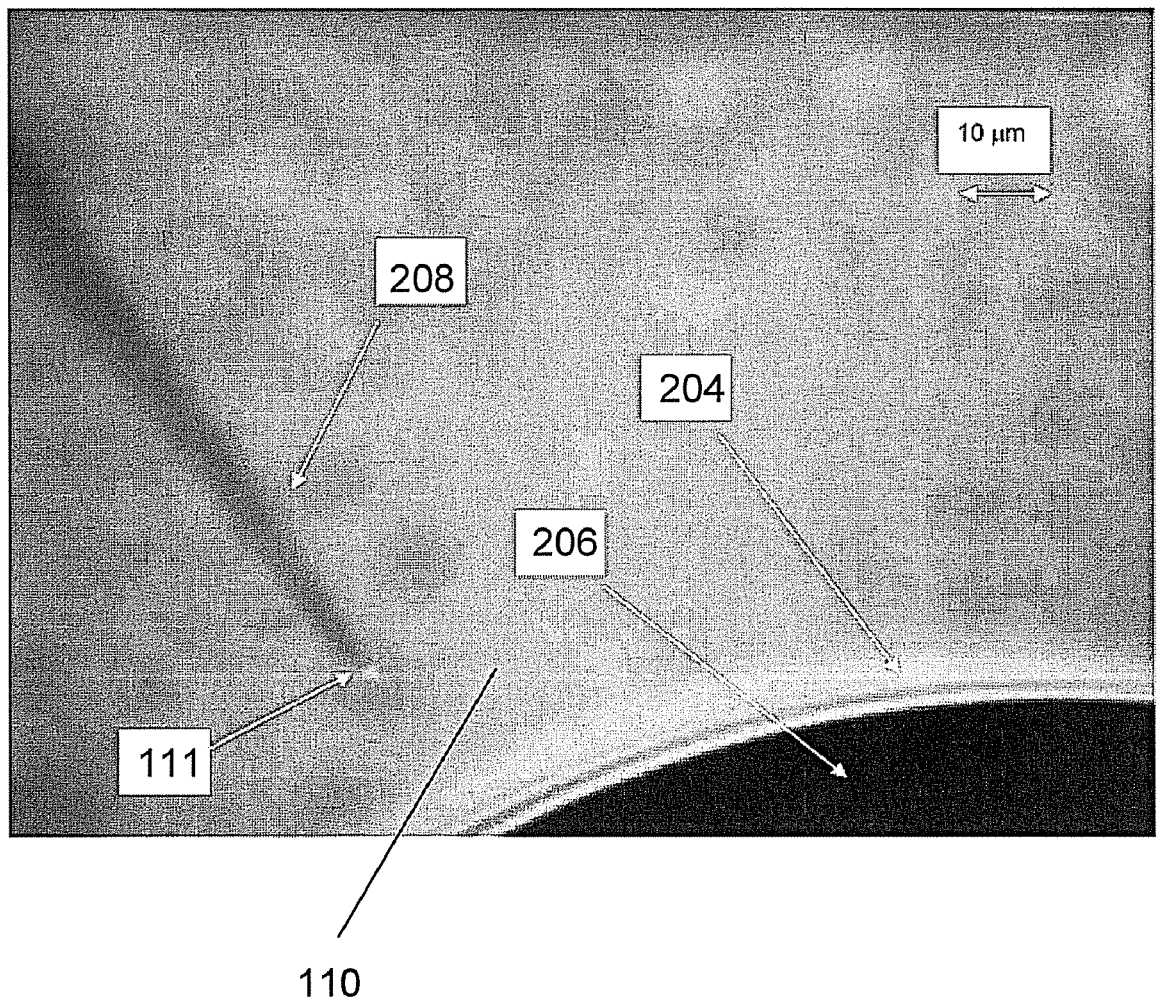
FIG. 9 illustrates a typical scenario of jet formation in liquid wherein the distance between the target location of the laser beam and the gas-liquid interface is shorter than 40 µm.

FIGS. 7-9 are CCD images showing various experimental scenarios of breakdowns in distilled water.

In these experiments, a sequence of 200 fs laser pulses are focused inside water through a transparent surface.

The laser pulse repetition rate in this experiment is 107 kHz, while the CCD camera frame rate is 20 Hz, therefore each image gives a picture averaged over a large number (~5000) of laser pulses.

Referring now to FIG. 7 illustrating a typical scenario of breakdown in liquid 110 (distilled water) and the formation of cavitation bubbles 302 with an irregular character.

In this case, the target location 111 of the laser beam is about 90 µm away from gas-liquid interface 204 (i.e., air-water interface) formed by bubble 206, and multiple laser pulses cause the formation of cavitation bubbles 302 with an irregular character (i.e., bubbles of various sizes form randomly with respect to space and time).

Referring now to FIG. 8 illustrating a typical scenario of jet formation in liquid 110 (distilled water). In this case, target location 111 of the laser beam is about 40 µm away from gas-liquid interface 204 (i.e., air-water interface) of gas bubble 206. In this case, jet 208 originates at target location 111 of the laser beam and directed away from gas-liquid interface 204 of gas bubble 206. Jet 208 propagates along the direction determined by the center of curvature of the surface and the target location 111 of the laser beam.

Referring now to FIG. 9 illustrating a scenario of jet formation in liquid 110 (distilled water) wherein target location 111 of the laser beam is in different position and even closer to gas-liquid interface 204 (i.e., air-water interface) of gas bubble 206 compared to the scenario illustrated in FIG. 8.

Since the target location 111 of the laser beam at another position to the gas-liquid interface 204 in this case (compared to the scenario illustrated in FIG. 8), the propagation direction of jet 208 is different than the propagation direction of the jet observed in FIG. 8.

Figure 10:
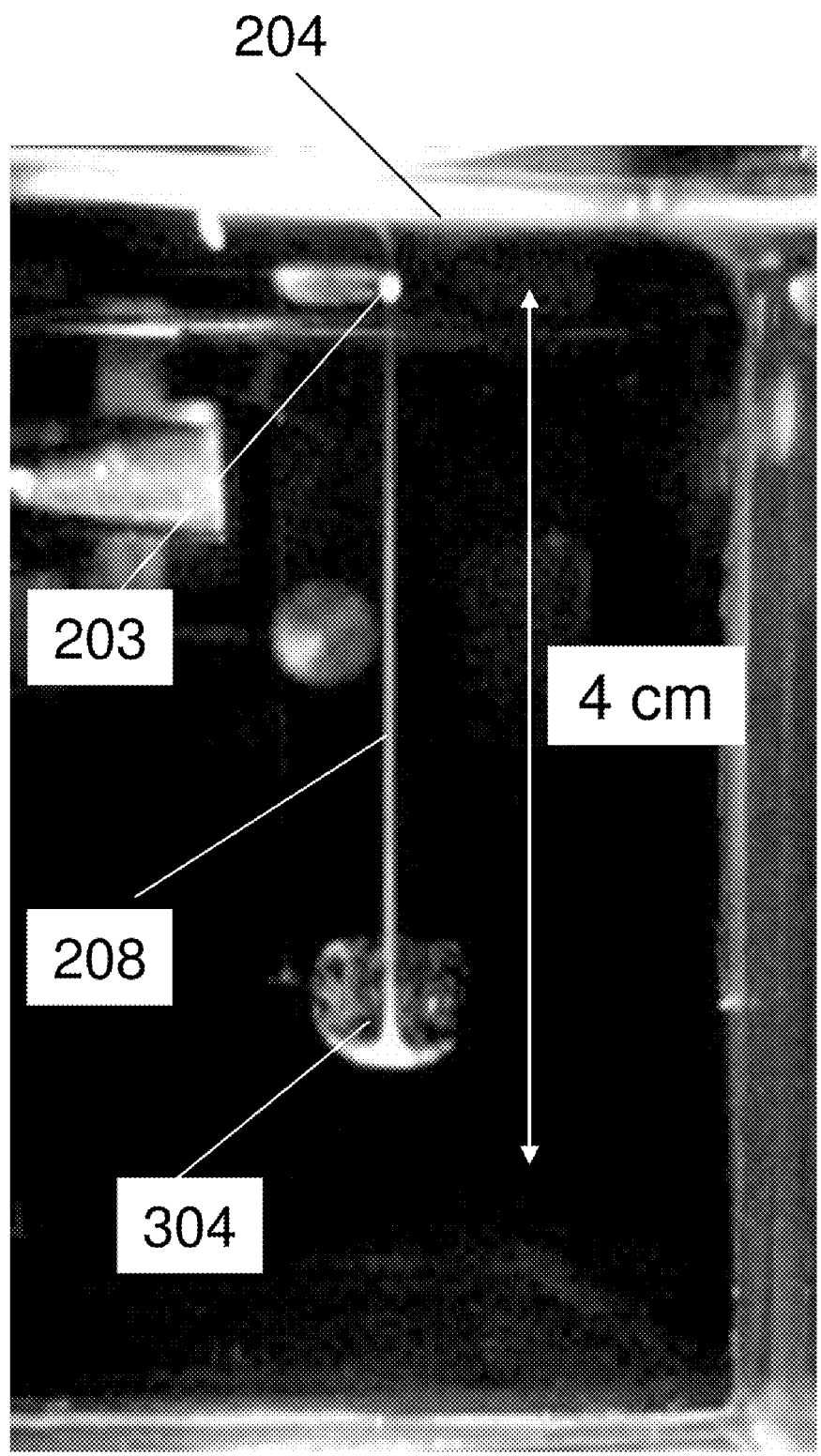
FIG. 10 illustrates a side-view of a jet formed in the vicinity of a substantially flat air-liquid interface.

FIG. 10 illustrates a side-view of jet 208 formed in the vicinity of a substantially flat air-water interface 204.

Jet 208 is produced by a beam comprising a sequence of 200 fs laser pulses with repletion rate of 107 kHz focused in the vicinity of a substantially flat air-water interface 204. An assembly 304 of bubbles can be seen at the end of jet 208.

As seen, jet 208 is initiated at target location 203. The direction of jet 208 is substantially perpendicular to the tangent to the gas-liquid interface 204.

Figure 11:
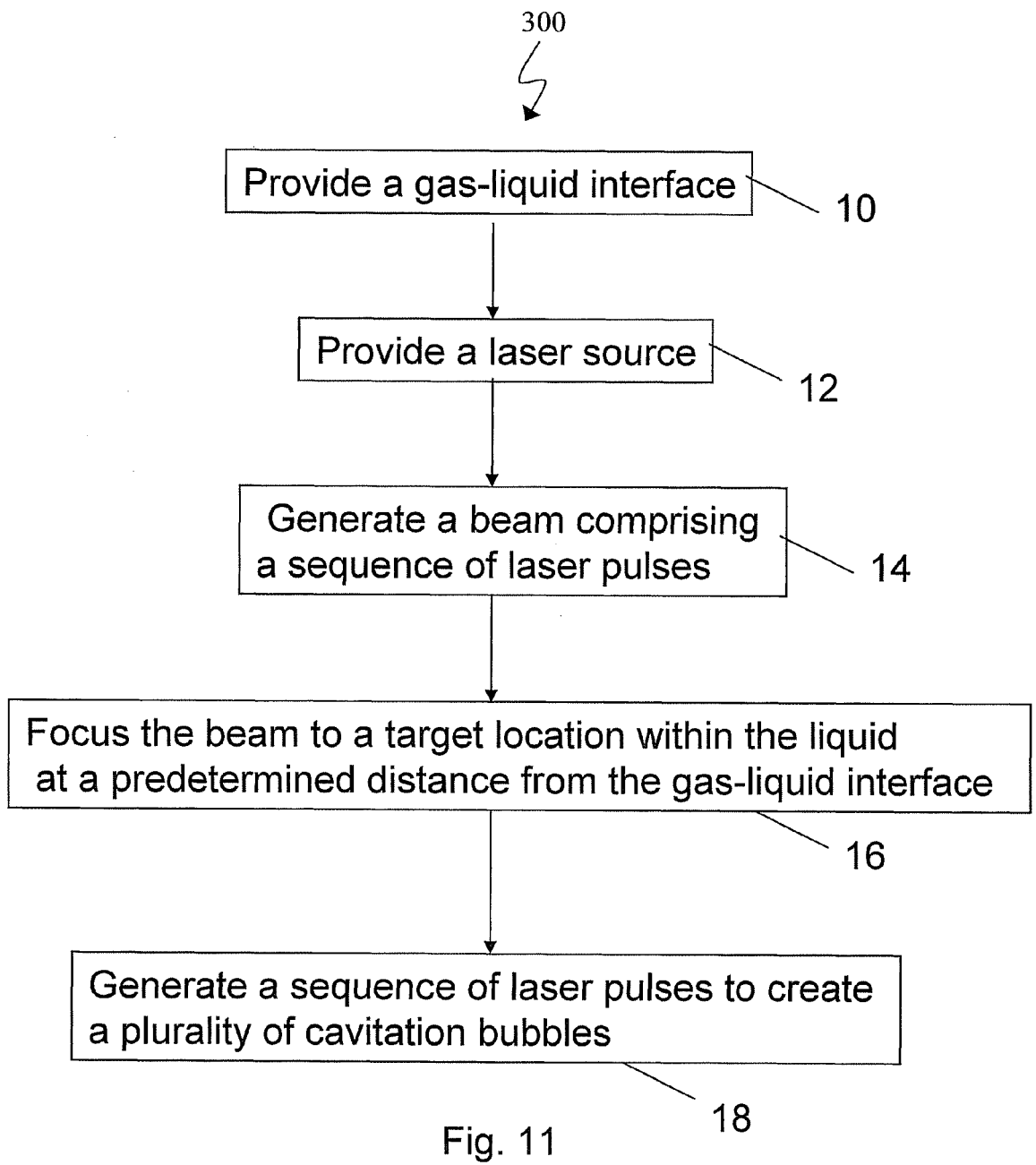
FIG. 11 is a flow chart illustrating stages of a method for inducing controllable jets in liquids in accordance with embodiments of the present invention.

FIG. 11 is a flow chart 300 illustrating stages of a method for inducing controllable jets in liquids in accordance with embodiments of the present invention. A method according to embodiments of the present invention comprises: providing a gas-liquid interface 10, providing a laser source 12, generating a beam comprising a sequence of laser pulses 14, focusing the beam to a target location within the liquid at a predetermined distance from the gas-liquid interface 16 and generating a sequence of laser pulses to create a plurality of cavitation bubbles 18.

In addition, it should be noted that the field of potential applications of laser induced controllable jets according to embodiments of the present invention is very wide ranging from local surface cleaning to microbiology and nanotechnology, and other applications as well.

While the invention has been described with respect to a limited number of embodiments, it will be appreciated that many variations, modifications and other applications of the invention may be made. Embodiments of the present invention may include other apparatuses for performing the operations herein. Such apparatuses may integrate the elements discussed, or may comprise alternative components to carry out the same purpose. It will be appreciated by persons skilled in the art that the appended claims are intended to cover all such modifications and changes as fall within the true spirit of the invention.

The invention claimed is:

1. A method for inducing a controllable jet in a transparent liquid, comprising:
   providing a gas-liquid interface;
   providing a laser source and generating a beam comprising a sequence of laser pulses;
   focusing said beam to a target location within the liquid at a predetermined distance from the gas-liquid interface and creating a plurality of cavitation bubbles; and
   wherein a time interval between the laser pulses within said sequence of pulses is longer than the cavitation time of the bubble and less than the decay time of cavitation flow generated by each bubble.

2. The method according to claim 1, wherein the step of generating a beam comprising a sequence of laser pulses includes generating laser pulses wherein each laser pulse is sufficient to create a cavitation bubble.

3. The method according to claim 1, wherein the predetermined distance is chosen to keep integrity of the gas-liquid interface and yielding a jet directed away from the gas-liquid interface.

4. The method according to claim 1, wherein the sequence of laser pulses comprises pulses with wavelength in the range of 0.3 to 3 µm, having a pulse energy ranging from 0.01 µJ to 100 mJ, a pulse width ranging from 10 fs to 30 ns and repetition rate ranging from 1 Hz to 100 MHz.

5. The method according to claim 1, wherein the step of creating a plurality of cavitation bubbles comprises creating a plurality of cavitation bubbles, so that each bubble moves away from the target location before the next bubble is created.

6. The method according to claim 1, wherein the gas-liquid interface is an air-water interface.

7. The method according to claim 1, wherein the gas-liquid interface is a liquid vapor-liquid interface.

8. The method according to claim 1, wherein the gas-liquid interface is an inert gas-water interface.

9. The method according to claim 1, wherein the gas-liquid interface is substantially flat.

10. The method according to claim 1, wherein the gas-liquid interface is curved.

11. The method according to claim 1, wherein the step of providing the gas-liquid interface in the liquid comprises providing a transparent surface atop a container filled with the liquid and providing a gas bubble beneath the transparent surface, the gas bubble defining the gas-liquid interface.

12. The method according to claim 1, wherein the step of providing the gas-liquid interface in the liquid comprises providing a solid holder in a container filled with the liquid and providing a gas bubble fixed on said solid holder defining the gas-liquid interface.

13. The method according to claim 12, wherein said solid holder is a needle.

14. The method according to claim 1, wherein the step of providing the gas-liquid interface comprises providing a liquid drop on a surface, the liquid drop defining the gas-liquid interface.

15. The method according to claim 1, wherein the step of providing the gas-liquid interface comprises providing a capillary in a container filled with the liquid and a pump for inflating a gas bubble through said capillary creating the gas-liquid interface.

16. The method according to claim 1 comprising providing relative displacement between the target location and the gas-liquid interface for controlling the length and direction of propagation of the jet.

17. The method according to claim 1, further comprising varying a property of the gas-liquid interface to control the jet.

18. The method according to claim 17, wherein the property of the gas-liquid interface is selected from a group of properties including curvature and distance from the target location.

19. An apparatus for inducing a controllable jet in a transparent liquid, the apparatus comprising:
- a support of liquid with a gas-liquid interface;
- a laser source for generating a beam comprising a sequence of laser pulses;
- a focusing optics for focusing a said beam to a target location within the liquid at a predetermined distance for creating a plurality of cavitation bubbles, yielding a jet directed away from the gas-liquid interface; wherein a time interval between the laser pulses within said sequence of pulses is longer than the cavitation time of the bubble and less than the decay time of cavitation flow generated by each bubble; and
- a relative displacement facilitator for facilitating relative displacement between the objective focal point and the gas-liquid interface for setting a predetermined distance between the objective focal point and the gas-liquid interface.

20. The apparatus according to claim 19, further provided with a facilitator for varying a property of the gas-liquid interface selected from a group of properties including a curvature of the gas-liquid interface and the distance of the target location from the gas-liquid interface.

21. The apparatus according to claim 19, wherein the sequence of laser pulses comprises pulses with wavelength in the range of 0.3 to 3 $\mu$m, having a pulse energy ranging from 0.01 $\mu$J to 100 mJ, a pulse width ranging from 10 fs to 30 ns and repetition rate ranging from 1 Hz to 100 MHz.

* * * * *